United States Patent
Iwano et al.

(10) Patent No.: US 9,753,020 B2
(45) Date of Patent: Sep. 5, 2017

(54) GAS SENSOR ELEMENT, GAS SENSOR, AND METHOD OF MANUFACTURING GAS SENSOR ELEMENT

(71) Applicant: NGK SPARK PLUG CO., LTD., Nagoya-shi, Aichi (JP)

(72) Inventors: Toru Iwano, Komaki (JP); Masaki Onkawa, Konan (JP); Tatsuhiko Muraoka, Komaki (JP); Shun Sakuma, Inuyama (JP); Shigehiro Ohtsuka, Gifu (JP); Masaki Mizutani, Niwa-gun (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 243 days.

(21) Appl. No.: 14/525,949

(22) Filed: Oct. 28, 2014

(65) Prior Publication Data
US 2015/0114085 A1    Apr. 30, 2015

(30) Foreign Application Priority Data
Oct. 29, 2013    (JP) ................................. 2013-224285

(51) Int. Cl.
*G01N 33/00*    (2006.01)
*B05D 1/18*    (2006.01)
(Continued)

(52) U.S. Cl.
CPC ........... *G01N 33/0027* (2013.01); *B05D 1/18* (2013.01); *B05D 1/36* (2013.01); *B05D 3/0254* (2013.01);
(Continued)

(58) Field of Classification Search
CPC ............. G01N 33/0027; G01N 27/407; G01N 27/4078; G01N 27/409
See application file for complete search history.

(56) References Cited

U.S. PATENT DOCUMENTS

| 7,241,370 B2 * | 7/2007 | Taguchi ............. G01N 27/4077 204/428 |
| 2003/0159928 A1 | 8/2003 | Kojima et al. |
| 2007/0175267 A1 * | 8/2007 | Yamauchi ............ G01N 27/407 73/31.05 |

FOREIGN PATENT DOCUMENTS

| JP | 2003-322632 A | 11/2003 |
| JP | 2012-168030 A | 9/2012 |

* cited by examiner

*Primary Examiner* — R. A. Smith
*Assistant Examiner* — John M Royston
(74) *Attorney, Agent, or Firm* — Stites & Harbison, PLLC; Jeffrey A. Haeberlin; James R. Hayne (57) ABSTRACT

A gas sensor element has a protection layer smaller in heat capacity than a conventional protection layer formed by a dipping process. A gas sensor includes the gas sensor element. The gas sensor element is manufactured by a method of manufacturing. The gas sensor element includes at least one space formed between a protection layer and an element body. The space is positioned over at least one of four vertexes of a forward end of the element body at a location at which the thickness of the protection layer is likely to become small. Therefore, it is possible to restrain breakage of the vertexes of the forward end of the element body which could otherwise result from thermal shock stemming from adhesion of water. The protection layer of the gas sensor element can be reduced in thickness and thus in heat capacity as compared with a conventional protection layer.

10 Claims, 8 Drawing Sheets

(51) Int. Cl.
*B05D 1/36* (2006.01)
*B05D 3/02* (2006.01)
*G01N 27/409* (2006.01)
*G01N 27/407* (2006.01)

(52) U.S. Cl.
CPC ......... *G01N 27/409* (2013.01); *G01N 27/407* (2013.01); *G01N 27/4078* (2013.01)

FIG. 9

GAS SENSOR ELEMENT, GAS SENSOR, AND METHOD OF MANUFACTURING GAS SENSOR ELEMENT

CROSS REFERENCE TO RELATED APPLICATIONS

The present application claims priority to Japanese Patent Application No. 2013-224285, which was filed on Oct. 29, 2013, the disclosure of which is herein incorporated by reference in its entirety.

BACKGROUND OF THE INVENTION

Field of the Invention

The present invention relates to a gas sensor element for detecting a particular gas contained in gas to be measured, a gas sensor having the gas sensor element, and a method of manufacturing the gas sensor element.

Description of Related Art

A conventionally known gas sensor having a gas sensor element for detecting a particular gas contained in gas to be measured is, for example, an oxygen sensor installed in an exhaust flow path, such as an exhaust pipe, of an internal combustion engine and utilized in controlling combustion of the internal combustion engine through detection of an oxygen concentration in exhaust gas. The oxygen sensor has, for example, a tubular metallic shell and a plate-like gas sensor element held in the metallic shell.

The gas sensor element includes a longitudinally extending plate-like element body, and a protection layer formed of a porous material and provided on the surface of the element body. The element body includes a detecting section provided in a longitudinally forward region thereof and adapted to detect a particular gas contained in gas to be measured. The protection layer is provided in a longitudinally forward end region of the element body in such a manner as to cover at least the detecting section.

The protection layer is provided for protecting the element body. Direct adhesion of condensed water may break the heated element body by thermal shock. Thus, by means of provision of the protection layer for restraining direct adhesion of condensed water or the like to the element body, breakage of the element body can be restrained. The protection layer has a certain thickness for allowing condensed water to evaporate before reaching the element body.

A known method of forming the protection layer of the gas sensor element is a dipping process in which a forward end portion of the element body is dipped in slurry prepared by mixing ceramic powder, water, and a pore-forming agent (e.g., carbon powder) (refer to Patent Document 1). The slurry applied to the element body undergoes heat treatment and becomes the protection layer.

RELATED ART DOCUMENTS

Patent Document 1 is Japanese Patent Application Laid-Open (kokai) No. 2003-322632.

BRIEF SUMMARY OF THE INVENTION

However, the above-mentioned dipping process involves the following problem: since the protection layer reduces in thickness at particular portions (particularly, in the vicinity of four vertexes of the forward end of the element body), in order to secure a sufficient thickness of the protection layer at those particular portions, dipping must be performed a plurality of times.

At this time, a plurality of times of dipping imparts an excess thickness to those portions of the protection layer which could have a sufficient thickness of the protection layer by a single time of dipping. Thus, the overall volume of the protection layer increases; accordingly, heat capacity of the protection layer increases, resulting in a wasteful increase in power consumption of a heater, along with an increase in time required for activating the sensor element.

A conceivable measure to cope with the above problem is utilization of a spraying process for spraying slurry on the surface of the element body with a spray after application of the slurry by a single time of dipping, at those particular portions which fail to have a sufficient thickness by the single time of dipping.

However, the spraying process is apt to involve waste of slurry; specifically, since slurry is sprayed in the form of mist, some slurry drops without being applied to the element body. Also, the spraying process involves the following problem: since the amount of spraying per unit time is small, and thus working time of spraying becomes long, the step of forming the protection layer becomes troublesome.

In view of the foregoing problem, an object of the present invention is to provide a gas sensor element whose protection layer is smaller in heat capacity than a conventional protection layer formed by a dipping process, and to provide a gas sensor having the gas sensor element as well as a method of manufacturing the gas sensor element.

According to one aspect of the present invention, a gas sensor element includes a rectangular-parallelepiped element body and a porous protection layer. The element body extends in a longitudinal direction and has, in its forward end region, a forward end surface and four side surfaces defining four vertexes. The element body includes a detecting section for detecting a particular gas (i.e., a component) contained in gas (i.e., a mixture) to be measured. The porous protection layer is located (i.e., provided) on the forward end surface and the four side surfaces of the element body in such a manner as to cover at least the detecting section. The porous protection layer has a largest thickness at a place on the four side surfaces of the element body.

The gas sensor element has at least one space formed to separate the element body and the protection layer (i.e., the element body and the protection layer define the at least one space therebetween), the space being provided only in a forward region located forward of the place on the side surfaces of the element body where the protection layer has its largest thickness.

The space is provided on (i.e. positioned over) at least one of the four vertexes of a forward end of the element body such that the space extends over three surfaces of the element body which define the one of the four vertexes, and the protection layer is in contact with at least a portion of the forward end surface and is in contact with at least a portion of the four side surfaces in the forward region.

In the thus-configured gas sensor element, the space for separating the element body and the protection layer is provided at the vertex of the forward end of the element body, at which the thickness of the protection layer is likely to become small, such that the space extends over three surfaces of the element body which define the vertex. By virtue of this, even when the thickness of the protection layer is small in the vicinity of the vertex, it is possible to restrain breakage of the vertex of the forward end of the element body which could otherwise result from thermal shock stemming from adhesion of water. This is because the space provided on the vertex causes condensed water adhering to the protection layer to penetrate into the protection layer while detouring the space, to thereby prevent the condensed water from reaching the vertex.

That is, the protection layer of the gas sensor element can be reduced in thickness and thus in heat capacity as compared with a conventional protection layer formed by a dipping process.

Also, the space is formed only in the forward region located forward of the place on the side surfaces of the element body where the protection layer has its largest thickness. By virtue of this feature, it is possible to prevent condensed water from reaching the vertex by the space, and is also possible to restrain deterioration in adhesion between the protection layer and the element body in a rear region located rearward of the place on the side surfaces of the element body where the protection layer has its largest thickness.

Additionally, the protection layer is in contact with at least a portion of the forward end surface of the element body and is in contact with at least a portion of the four side surfaces in the forward region. Thus, although the space formed in such a manner as to separate the element body and the protection layer is provided in the forward region, deterioration in adhesion between the protection layer and the element body can be restrained even in the forward region.

Thus, the present invention can implement the gas sensor element having the protection layer whose heat capacity is smaller than that of a conventional protection layer formed by a dipping process.

The "substantially rectangular-parallelepiped element body" appearing in the present invention encompasses not only a rectangular-parallelepiped element body but also an element body in the shape of a rectangular parallelepiped whose edges are chamfered. In the case of an element body having chamfered edges, "four vertexes of a forward end of the element body" indicate ridgelines defined by the chamfers and the forward end surface.

No particular limitation is imposed on provision of the space, so long as the space is provided on at least one of four vertexes of the forward end of the element body. The space may be provided on a single vertex, or the spaces may be provided on the four vertexes, respectively. Furthermore, the spaces may be provided on the vertexes in one-to-one relation, or a single space may be provided over a plurality of vertexes.

It is sufficient that the protection layer is in contact with at least a portion of the forward end surface of the element body. Therefore, the protection layer may be in contact with a portion of the forward end surface or be in contact with the entire forward end surface excluding the space.

It is sufficient that the protection layer is in contact with at least a portion of the four side surfaces in the forward region. Therefore, the protection layer may be in contact with one side surface in the forward region or be in contact with each of the four side surfaces in the forward region.

In the above-described gas sensor element, the protection layer may be in contact with at least a portion of each of the four side surfaces in the forward region.

In the case where the protection layer is in contact with at least a portion of each of the four side surfaces in the forward region, it is possible to further restrain deterioration in adhesion between the protection layer and the side surfaces of the element body in the forward region. Thus, separation of the protection layer from the element body becomes more unlikely to arise.

In the above-described gas sensor element, the element body may be in contact with the protection layer through a portion of the forward end surface and portions of the side surfaces in the forward region, and the total surface area of the portion of the forward end surface and the portions of the side surfaces may be half of the total surface area of the forward end surface and the four side surfaces in the forward region.

In this case, a sufficiently large contact area can be secured between the element body and the protection layer in the forward region. Therefore, separation of the protection layer from the element body becomes more unlikely to arise.

In the above-mentioned gas sensor element, one space may be provided on (i.e. positioned over) only one of the four vertexes.

That is, in this gas sensor element, since one space is provided on only one vertex, a single space is not formed above a plurality of vertexes. Therefore, it is possible to prevent the space from occupying an excessively large area on the outer surface of the forward region of the element body, to thereby secure a sufficiently large contact area between the element body and the protection layer.

Thus, according to this gas sensor element, since a large contact area can be secured between the element body and the protection layer, separation of the protection layer from the element body can be further restrained.

In the above-mentioned gas sensor element, a plurality of (i.e., at least two) spaces may be provided.

In the case where a plurality of spaces are provided, it is possible to prevent condensed water from reaching the plurality of vertexes of the element body, to thereby restrain breakage of the element body which could otherwise result from thermal shock stemming from adhesion of water.

Notably, in the above-described gas sensor element, the space may be provided on each of at least two diagonally located vertexes of the four vertexes of the forward end of the element body.

In the above-mentioned gas sensor element, the maximum width of the space measured from the vertex in the width direction of the element body may be less than half the width of the element body.

In the case where the maximum width of the space is less than half the width of the element body, it is possible to prevent the space from occupying an excessively large area on the outer surface of the forward region of the element body, to thereby secure a sufficiently large contact region on the outer surface of the element body in which the element body is in contact with the protection layer.

In the above-mentioned gas sensor element, the maximum thickness of the space measured from the vertex in the thickness direction of the element body may be less than half the thickness of the element body.

In the case where the maximum thickness of the space is less than half the thickness of the element body, it is possible to prevent the space from occupying an excessively large area on the outer surface of the forward region of the element body, to thereby secure a sufficiently large contact region on the outer surface of the element body in which the element body is in contact with the protection layer.

According to another aspect of the present invention, a gas sensor includes the gas sensor element according to any one of the above-mentioned gas sensor elements and adapted to detect the particular gas contained in the gas to be measured.

The gas sensor comprises any one of the above-mentioned gas sensor elements in which there can be restrained breakage of the vertexes of the forward end of the element body which could otherwise result from thermal shock stemming from adhesion of water. Also, the protection layer of the gas sensor element can be smaller in thickness than a conventional protection layer formed by a dipping process and is thus smaller in heat capacity than the conventional protection layer.

Therefore, the gas sensor of the present invention can be configured to have the gas sensor element whose protection layer is smaller in heat capacity than a conventional protection layer.

Another aspect of the present invention, is a method of manufacturing a gas sensor element, as discussed above, which includes a substantially rectangular-parallelepiped element body extending in a longitudinal direction and having, in its forward end region, a detecting section for detecting a particular gas contained in gas to be measured, and a porous protection layer provided on a forward end surface and side surfaces of the element body in such a manner as to cover at least the detecting section.

The gas sensor element manufactured by this manufacturing method has at least one space formed to separate the element body and the protection layer, the space being provided only in a forward region located forward of a place on the side surfaces of the element body where the protection layer has its largest thickness. The space is provided on at least one vertex of four vertexes of a forward end of the element body such that the space extends over three surfaces of the element body which define the vertex. The protection layer is in contact with at least a portion of the forward end surface and is in contact with at least a portion of the four side surfaces in the forward region.

The method of manufacturing the gas sensor element includes a solvent disposing step of disposing a volatile solvent on an outer surface of the element body in a region where the space is to be formed, a protection layer forming step of forming, on the element body on which the volatile solvent remains, a green protection layer which is to become the protection layer through heat treatment, in such a manner as to cover at least the detecting section, and a heat treatment step of performing heat treatment on the element body on which the green protection layer is formed, thereby forming the protection layer, wherein the volatile solvent is volatilized in a period from start of the solvent disposing step to end of the heat treatment step, thereby forming the space.

That is, the space can be formed between the element body and the protection layer in the course of a series of the following steps as a result of volatilization of the volatile solvent: the volatile solvent is disposed on the outer surface of the element body in a region where the space is to be formed; the green protection layer is formed on the element body on which the volatile solvent remains; and heat treatment is performed on the element body on which the green protection layer is formed, thereby forming the protection layer.

According to the method of manufacturing the gas sensor element which uses the volatile solvent and comprises the solvent disposing step, the protection layer forming step, and the heat treatment step, the gas sensor element having the space between the element body and the protection layer can be easily manufactured.

The present invention can implement a gas sensor element whose protection layer is smaller in heat capacity than a conventional protection layer formed by a dipping process.

Also, the gas sensor of the present invention can be configured to have the gas sensor element whose protection layer is smaller in heat capacity than a conventional protection layer.

Furthermore, the method of manufacturing the gas sensor element of the present invention can manufacture the gas sensor element which has the space between the element body and the protection layer and whose protection layer is smaller in heat capacity than a conventional gas sensor element.

BRIEF DESCRIPTION OF THE DRAWINGS

Illustrative aspects of the invention will be described in detail with reference to the following figures wherein.

DETAILED DESCRIPTION OF EXEMPLARY EMBODIMENTS OF THE INVENTION

Embodiments of the present invention will next be described with reference to the drawings.

The following embodiments will be described while referring to a full range air/fuel ratio sensor (hereinafter, may be referred to as merely the air/fuel ratio sensor), which is a kind of oxygen sensor among gas sensors. Specifically, the following description will refer to an air/fuel ratio sensor which is attached to an exhaust pipe of an internal combustion engine and which employs a gas sensor element (detecting element) for detecting a particular gas (oxygen) contained in gas to be measured; specifically, exhaust gas, for use in air/fuel ratio feedback control in the internal combustion engine.

A. First Embodiment 1-1. Overall Configuration

Figure 1:
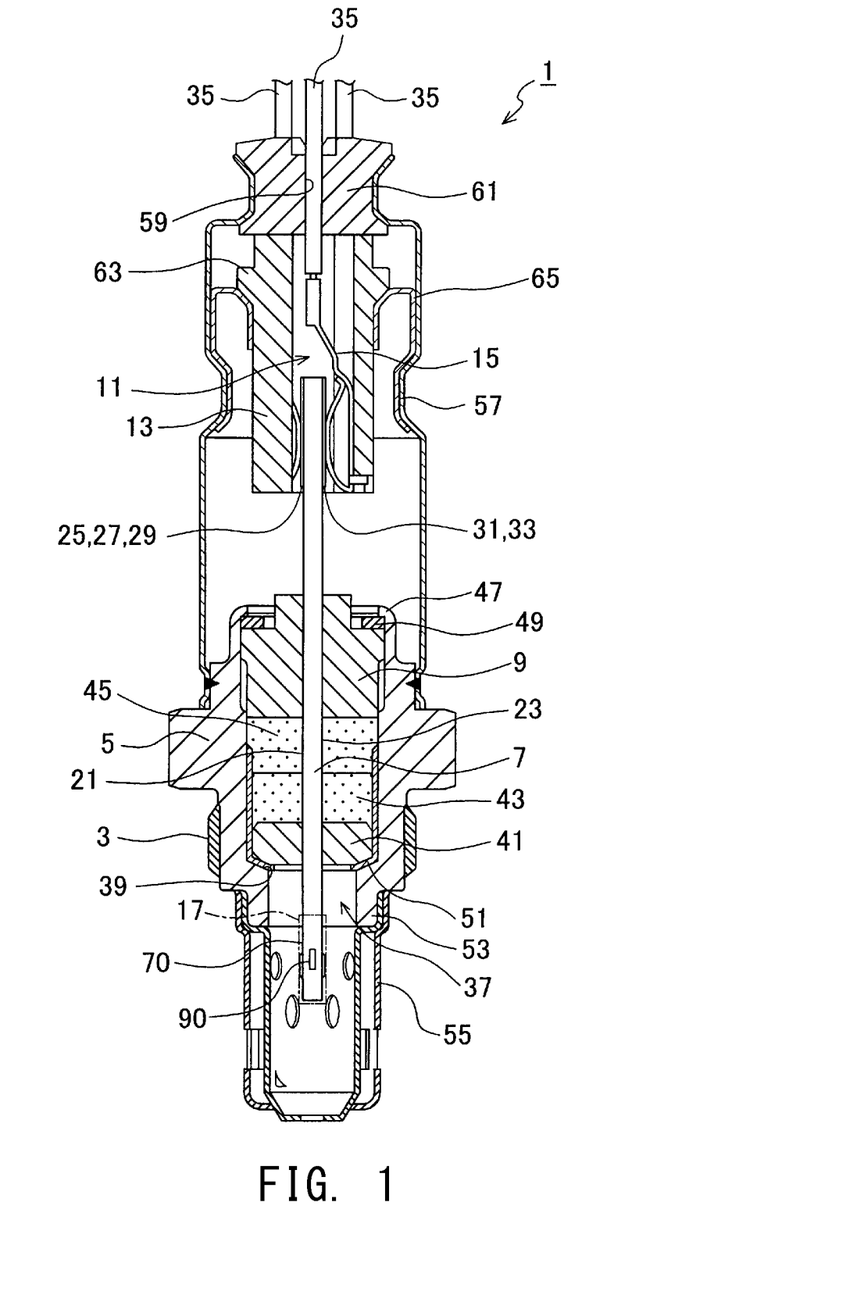
FIG. 1 is a sectional view of an air/fuel ratio sensor according to an embodiment of the present invention taken along an axial direction.

The overall configuration of an air/fuel ratio sensor which uses a gas sensor element of the present embodiment will be described with reference to FIG. 1. FIG. 1 is a sectional view showing the internal configuration of the air/fuel ratio sensor.

As shown in FIG. 1, an air/fuel ratio sensor 1 of the present embodiment includes a tubular metallic shell 5 having a threaded portion 3 formed on its outer surface and adapted to fix it to an exhaust pipe; a plate-like gas sensor element 7 extending in an axial direction (a longitudinal direction of the air/fuel ratio sensor 1, a vertical direction in FIG. 1); a tubular ceramic sleeve 9 disposed in such a manner as to radially surround the gas sensor element 7; an insulating contact member 13 (separator 13) which has an insertion hole 11 extending therethrough in the axial direction and which is disposed such that the inner wall surface of the insertion hole 11 surrounds a rear end portion of the gas sensor element 7; and five connection terminals 15 (FIG. 1 shows only two of them) disposed between the gas sensor element 7 and the separator 13.

As will be described in detail later, the gas sensor element 7 includes a rectangular-parallelepiped element body 70 extending in the longitudinal direction, and a porous protection layer 17 which covers a forward end portion of the element body 70. The element body 70 has a detecting section 90 provided in its forward end region and adapted to detect a particular gas contained in gas to be measured. Also, the gas sensor element 7 has electrode pads 25, 27, 29, 31, and 33 formed on the outer surface of its rear end portion (an upper end portion in FIG. 1, a longitudinally rear end portion); specifically, on a first main surface 21 and a second main surface 23 of the rear end portion (see FIGS. 2 and 3 for detail).

The connection terminals 15 are electrically connected to the electrode pads 25, 27, 29, 31, and 33, respectively, of the gas sensor element 7, and are also electrically connected to respective lead wires 35 extending into the sensor from outside, thereby forming electrical current paths through which electric current flows between an external device connected to the lead wires 35, and the electrode pads 25, 27, 29, 31, and 33.

The metallic shell 5 has a substantially tubular shape and is configured to have a through hole 37 extending therethrough in the axial direction and a ledge 39 protruding radially inward from the wall surface of the through hole 37. The metallic shell 5 holds the gas sensor element 7 inserted through the through hole 37 in such a manner that the detecting section 90 is disposed forward of the forward end of the through hole 37, while the electrode pads 25, 27, 29, 31, and 33 are disposed rearward of the rear end of the through hole 37.

Also, in the through hole 37 of the metallic shell 5, an annular ceramic holder 41, a talc ring 43, a talc ring 45, and the ceramic sleeve 9 are stacked rearward in this order in such a manner as to radially surround the gas sensor element 7.

A crimp packing 49 is disposed between the ceramic sleeve 9 and a rear end portion 47 of the metallic shell 5, while a metallic holder 51 for holding the talc ring 43 and the ceramic holder 41 is disposed between the ceramic holder 41 and the ledge 39 of the metallic shell 5. The rear end portion 47 of the metallic shell 5 is crimped in such a manner as to press forward the ceramic sleeve 9 through the crimp packing 49.

Furthermore, a protector 55 made of metal (e.g., stainless steel) and having a dual structure is attached to the outer circumference of a forward end portion 53 of the metallic shell 5 by, for example, welding and covers a protruding portion of the gas sensor element 7.

Meanwhile, an outer tube 57 is fixed to the outer circumference of a rear portion of the metallic shell 5. A grommet 61 having lead wire insertion holes 59 formed therein is disposed in a rear opening of the outer tube 57, and the five lead wires 35 (FIG. 1 shows three of them) are inserted through the respective lead wire insertion holes 59 and are electrically connected to the electrode pads 25, 27, 29, 31, and 33, respectively.

The separator 13 has a collar portion 63 formed along its outer circumference, and the collar portion 63 is fixed to the outer tube 57 through a holding member 65.

1-2. Configuration of Gas Sensor Element

Next, the configuration of the gas sensor element 7, which is an essential member of the present embodiment, will be described in detail with reference to FIGS. 2 to 5.

Figure 2:
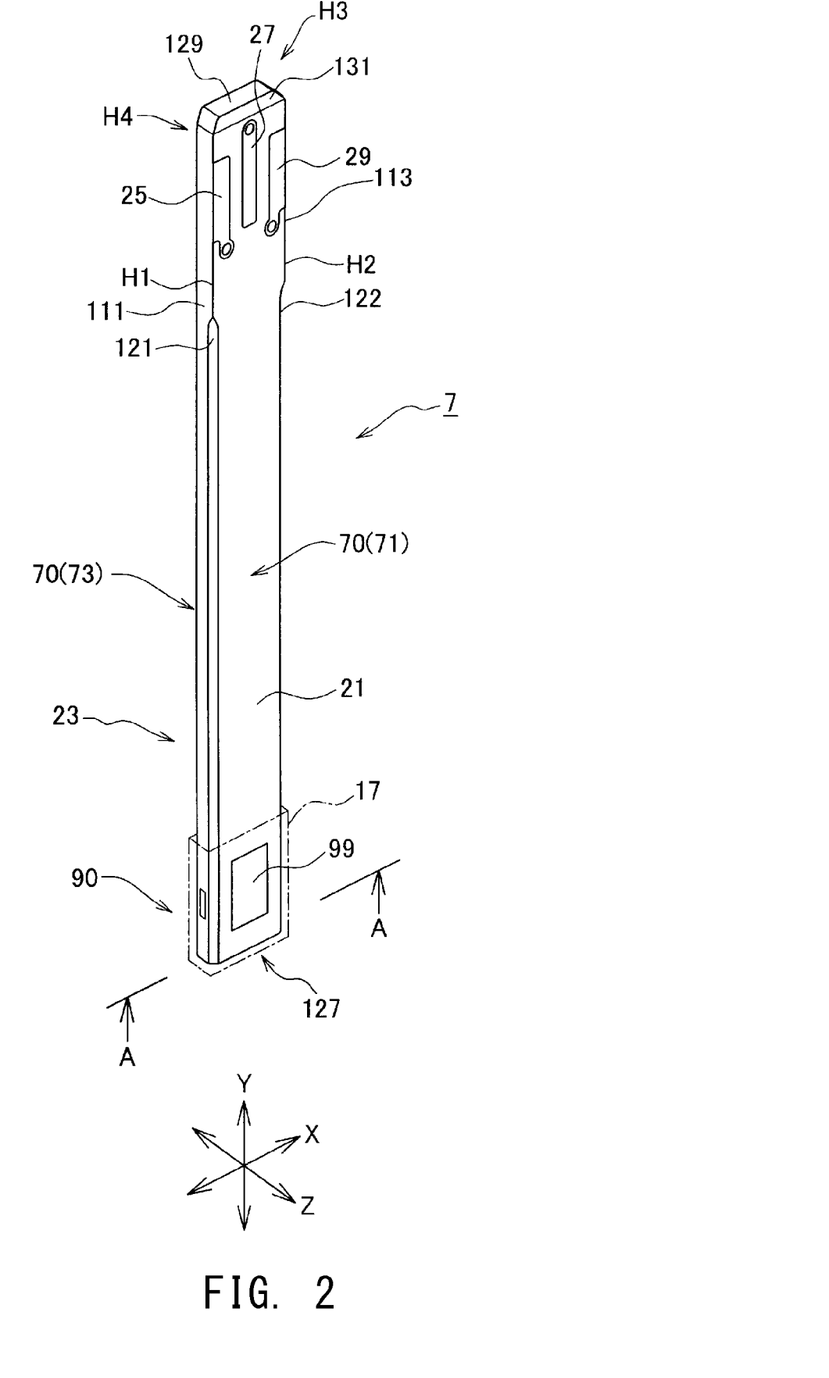
FIG. 2 is a perspective view showing a gas sensor element.

FIG. 2 is a perspective view showing the appearance of the gas sensor element 7.

As shown in FIG. 2, the gas sensor element 7 is an elongated plate member extending in the longitudinal direction (Y-axis direction). In FIG. 2, the longitudinal direction corresponds to the axial direction of the gas sensor. Also, in FIG. 2, a Z-axis direction is a thickness direction perpendicular to the longitudinal direction, and an X-axis direction is a width direction perpendicular to the longitudinal direction and to the thickness direction.

The gas sensor element 7 includes a rectangular-parallelepiped element body 70 extending in the longitudinal direction, and the porous protection layer 17 which covers a forward end portion (a lower end portion in FIG. 2) of the element body 70. The element body 70 is configured such that a plate-like element 71 extending in the longitudinal direction and a plate-like heater 73 extending in the longitudinal direction are laminated together. The element body 70 has the detecting section 90 provided in its forward end region and adapted to detect a particular gas contained in gas to be measured. The protection layer 17 is provided on a forward end surface 127 and side surfaces (the first main surface 21, the second main surface 23, a first side surface 111, and a second side surface 113) of the element body 70 in such a manner as to cover at least the detecting section 90.

Figure 3:
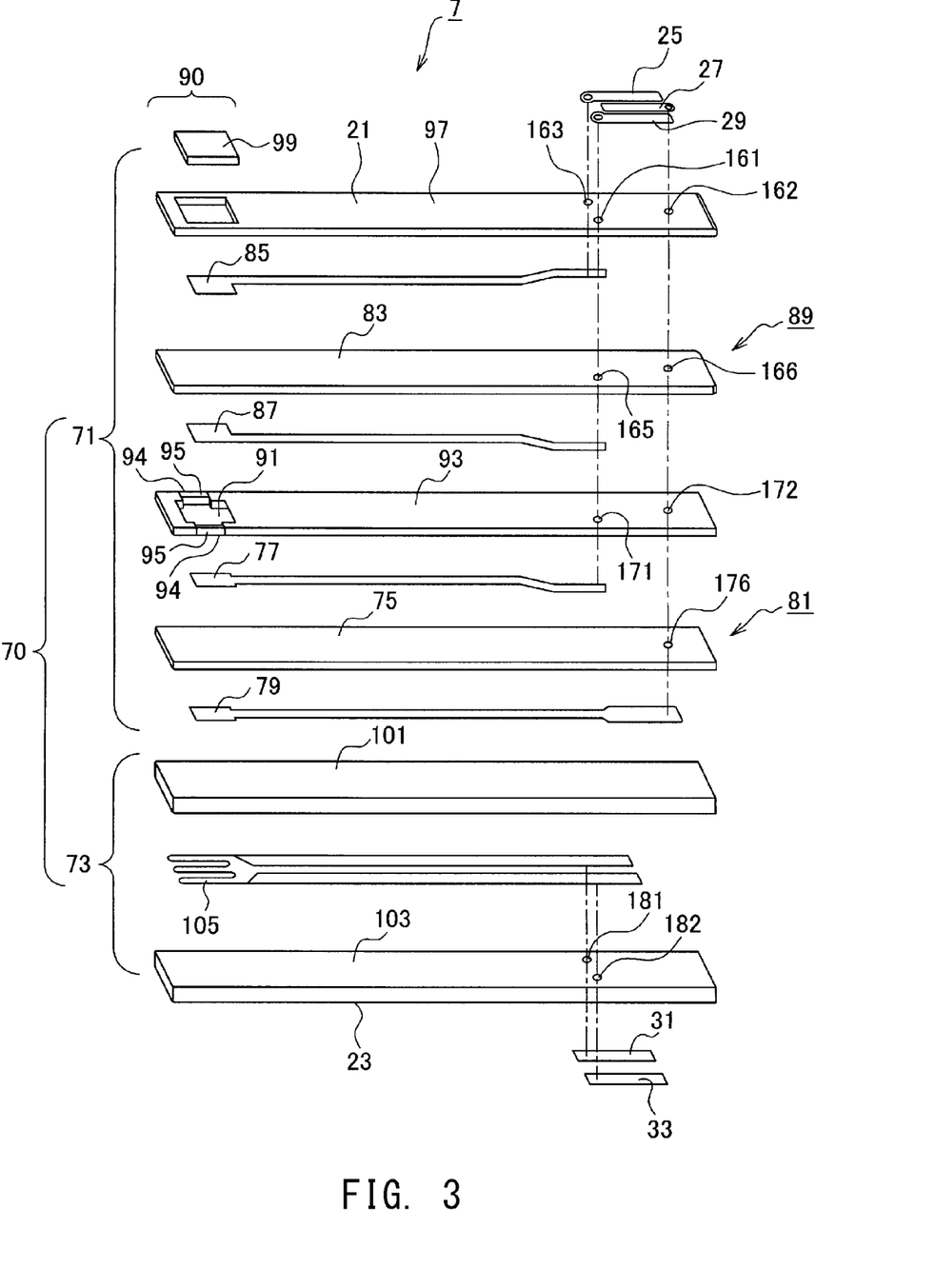
FIG. 3 is an exploded perspective view showing the gas sensor element.

FIG. 3 is an exploded perspective view showing the gas sensor element 7. FIG. 3 omits illustration of the protection layer 17 as well as a first long-side chamfer 121, a second long-side chamfer 122, a third long-side chamfer 123, and a fourth long-side chamfer 124, which will be described later.

As shown in FIG. 3 in an exploded condition, the element body 70 of the gas sensor element 7 includes the plate-like element 71 disposed on one side (upper side in FIG. 3) in a laminating direction and extending in the longitudinal direction, and the plate-like heater 73 disposed on a side (back side) opposite the element 71 and extending in the longitudinal direction.

The element 71 includes an oxygen concentration cell 81 configured such that porous electrodes 77 and 79 are formed on respective opposite sides of a solid electrolyte body 75; an oxygen pump cell 89 configured such that porous electrodes 85 and 87 are formed on respective opposite sides of a solid electrolyte body 83; and an insulating spacer 93 laminated between the two cells 81 and 89 and having a hollow gas measuring chamber 91 formed therein. The solid electrolyte bodies 75 and 83 are formed of zirconia which contains yttria as a stabilizer in solid solution, and the porous electrodes 77, 79, 85, and 87 are formed primarily of Pt.

The insulating spacer 93 in which the gas measuring chamber 91 is formed is formed primarily of alumina. The porous electrode 77 of the oxygen concentration cell 81 and the porous electrode 87 of the oxygen pump cell 89 are disposed in such a manner as to be exposed to the hollow gas measuring chamber 91.

The element 71 has two gas inlets 94 formed in respective sides thereof (sides of the insulating spacer 93). The gas inlets 94 serve as intakes of exhaust gas (gas to be measured) and communicate with the gas measuring chamber 91. Diffusion controlling portions 95 are formed in respective paths extending from the two gas inlets 94 to the gas measuring chamber 91. The diffusion controlling portions 95 are porous bodies formed of, for example, alumina and control diffusion of gas to be measured which flows into the gas measuring chamber 91. The diffusion controlling portions 95 are partially exposed from the gas inlets 94.

That is, in the gas sensor element 7, the gas inlets 94 are formed in the outermost surfaces of the element body 70 and face in two different directions, and the diffusion controlling portions 95 are exposed in the two different directions.

Furthermore, an insulating substrate 97 formed primarily of alumina is laminated on the first main surface 21 side (upper side in FIG. 3) of the element 71. The insulating substrate 97 has a ventilating portion 99 embedded therein, and the ventilating portion 99 is a porous body similar to the case of the diffusion controlling portions 95. The ventilating portion 99 allows the porous electrode 85 of the oxygen pump cell 89 to be exposed to gas to be measured.

The gas measuring chamber 91 is located in a forward end region (left end region in FIG. 3) of the element body 70. With respect to the longitudinal direction of the element 71, a region where the gas measuring chamber 91 is formed, and a region located forward of the gas measuring chamber 91 constitute the detecting section 90 for detecting oxygen.

Meanwhile, the heater 73 is formed such that a heat generating resistor pattern 105 formed primarily of Pt is sandwiched between insulating substrates 101 and 103 formed primarily of alumina.

The gas sensor element 7 has the three electrode pads 25, 27, and 29 formed on a rear end portion (right end portion in FIG. 3) of the first main surface 21, and the two electrode pads 31 and 33 formed on a rear end portion of the second main surface 23.

As shown in FIG. 3, the electrode pad 29 (right-hand electrode pad in FIG. 2) formed on the first main surface 21 is electrically connected to the porous electrode 77 of the oxygen concentration cell 81 exposed to the gas measuring chamber 91, through a through hole 161 provided in the insulating substrate 97, a through hole 165 provided in the solid electrolyte body 83, and a through hole 171 provided in the insulating spacer 93. The electrode pad 29 is also electrically connected to the porous electrode 87 of the oxygen pump cell 89 exposed to the gas measuring chamber 91, through the through hole 161 provided in the insulating substrate 97 and the through hole 165 provided in the solid electrolyte body 83. Thus, the porous electrode 77 and the porous electrode 87 are electrically connected to each other and thus have the same electrical potential.

Also, as shown in FIG. 3, another electrode pad (central electrode pad in FIG. 2) is electrically connected to the other porous electrode 79 of the oxygen concentration cell 81 through a through hole 162 provided in the insulating substrate 97, a through hole 166 provided in the solid electrolyte body 83, a through hole 172 provided in the insulating spacer 93, and a through hole 176 provided in the solid electrolyte body 75. Furthermore, as shown in FIG. 3, a further electrode pad 25 (left-hand electrode pad in FIG. 2) is electrically connected to the other porous electrode 85 of the oxygen pump cell 89 through a through hole 163 provided in the insulating substrate 97.

Also, as shown in FIG. 3, the electrode pads 31 and 33 are electrically connected to respective opposite ends of the heat generating resistor pattern 105 through holes 181 and 182, respectively, provided in the insulating substrate 103.

Referring back to FIG. 2, since the thus-configured gas sensor element 7 is an elongated, substantially rectangular-parallelepiped plate element, it has four edges (longitudinal ridgelines) H1, H2, H3, and H4 extending its longitudinal direction (Y-axis direction in FIG. 2).

More specifically, the gas sensor element 7 has four outer walls extending its longitudinal direction; i.e., the first main surface 21 and the second main surface 23, and the first side surface 111 and the second side surface 113 in contact with the first main surface 21 and the second main surface 23. Also, the gas sensor element 7 has the first edge H1, which is a ridgeline between the first main surface 21 and the first side surface 111; the second edge H2, which is a ridgeline between the first main surface 21 and the second side surface 113; the third edge H3, which is a ridgeline between the second main surface 23 and the second side surface 113; and the fourth edge H4, which is a ridgeline between the second main surface 23 and the first side surface 111.

Figure 4:
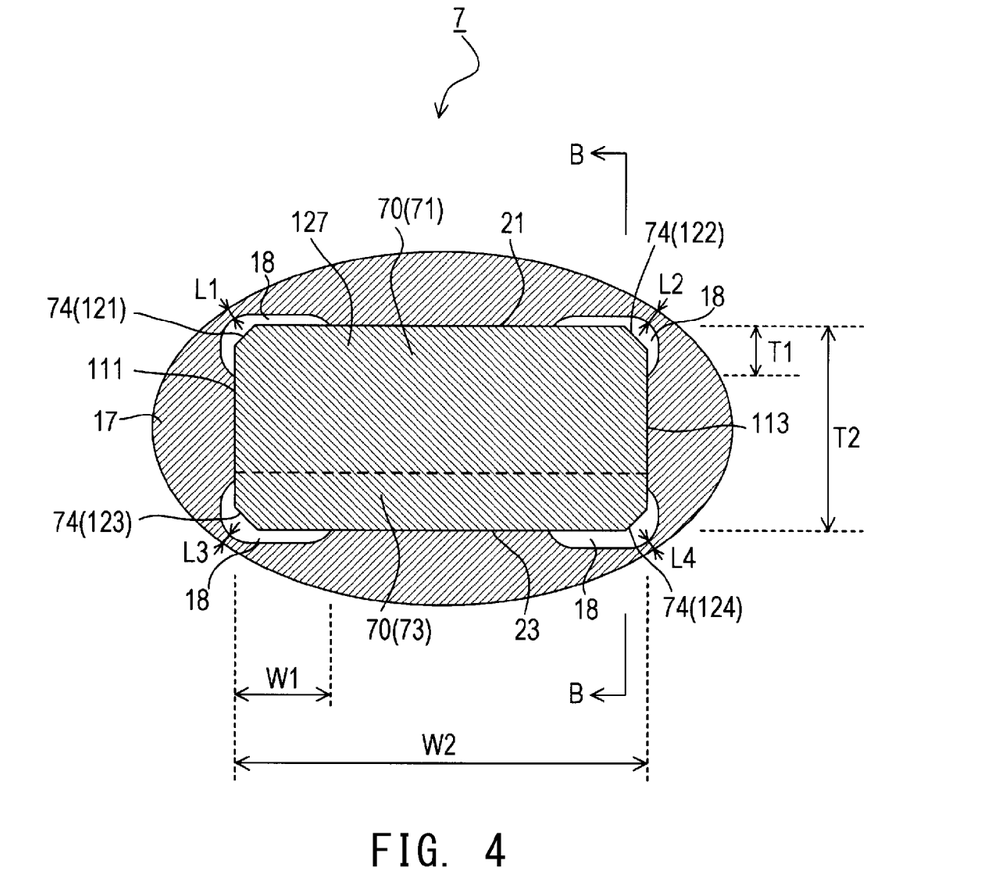
FIG. 4 is a sectional view of the gas sensor element taken along line AA of FIG. 2.

The first edge H1, the second edge H2, the third edge H3, and the fourth edge H4 are chamfered by 0.2 mm, thereby providing a first long-edge chamfer 121, a second long-edge chamfer 122, a third long-edge chamfer 123 (see FIG. 4), and a fourth long-edge chamfer 124 (see FIG. 4). In FIG. 2, since the third long-edge chamfer 123 and the fourth long-edge chamfer 124 are invisible, their illustration with reference numerals is omitted.

The gas sensor element 7 is also chamfered at four ridgelines of its rear end surface 129 (upper end surface in FIG. 2), thereby forming rear end chamfers 131 while leaving the central rear end surface 129 (perpendicular to the longitudinal direction).

Next will be described spaces 18 formed between the element body 70 and the protection layer 17 of the gas sensor element 7.

Figure 5:
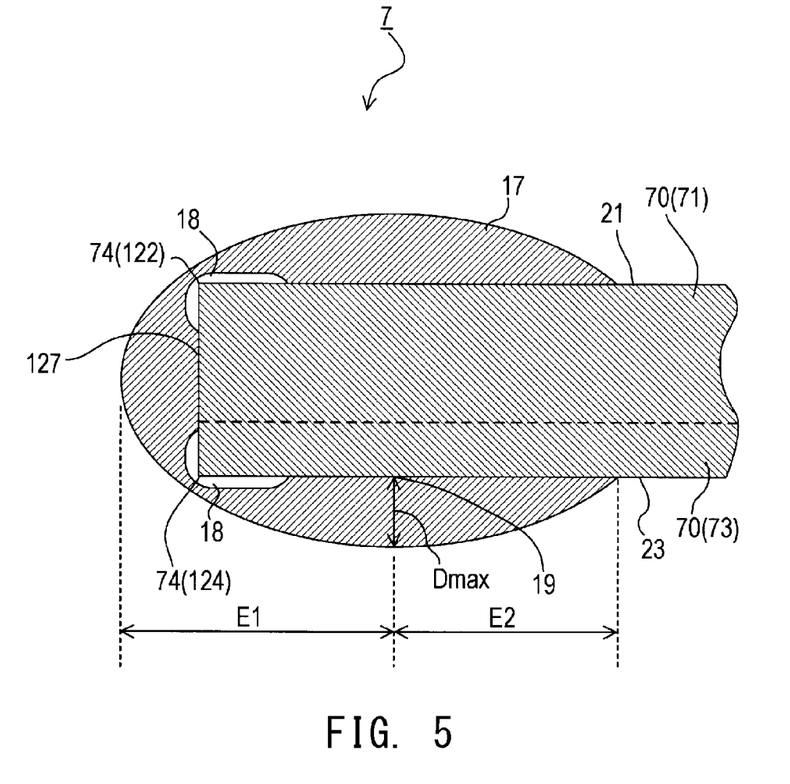
FIG. 5 is a sectional view of the gas sensor element taken along line B-B of FIG. 4.

FIG. 4 is a sectional view of the gas sensor element 7 taken along line A-A of FIG. 2. FIG. 5 is a sectional view of the gas sensor element 7 taken along line B-B of FIG. 4.

The protection layer 17 is formed of porous alumina and covers at least the detecting section 90 of the element body 70. The spaces 18 are formed between the protection layer 17 and the element body 70 so as to separate the protection layer 17 and the element body 70.

The number of the spaces 18 is at least four. The spaces 18 are formed such that they correspond to four vertexes 74 of the forward end surface 127 of the element body 70. Each space 18 is formed on a single vertex 74 such that it extends over three surfaces of the element body 70 which define the single vertex 74. For example, of the four spaces 18 shown in FIG. 4, the upper left space 18 is provided on a single vertex 74 such that the space 18 extends over the first main surface 21, the forward end surface 127, and the first side surface 111 of the element body 70.

Since the element body 70 of the present embodiment has the first long-edge chamfer 121, the second long-edge chamfer 122, the third long-edge chamfer 123, and the fourth long-edge chamfer 124, each of the four vertexes 74 assumes the form of a ridgeline defined by the forward end surface 127 and each of the first long-edge chamfer 121, the second long-edge chamfer 122, the third long-edge chamfer 123, and the fourth long-edge chamfer 124.

Also, as shown in FIG. 5, the spaces 18 are provided on the side surfaces (the first main surface 21, the second main surface 23, the first side surface 111, and the second side surface 113) of the element body 70 only in a forward region E1 located forward of a place 19. The place 19 on the element body 70 is a place on the side surfaces (the first main surface 21, the second main surface 23, the first side surface 111, and the second side surface 113) of the element body 70 where the protection layer 17 has its largest thickness Dmax.

The gas sensor element 7 has the spaces 18 provided on those respective vertexes 74 of the forward end surface 127 of the element body 70 at which the thickness of the protection layer 17 is apt to reduce, and extending over three surfaces of the element body 70 which define each of the vertexes 74. Thus, the element body 70 and the protection layer 17 are separated. Therefore, even though the thicknesses L1 to L4 of the protection layer 17 in the vicinity of the vertexes 74 are small, there can be restrained breakage of the vertexes 74 of the forward end of the element body 70 which could otherwise result from thermal shock stemming from adhesion of water. This is because the spaces 18 provided on the vertexes 74 cause condensed water adhering to the protection layer 17 to penetrate into the protection layer 17 while detouring the spaces 18, to thereby prevent the condensed water from reaching the vertexes 74.

Also, the spaces 18 are provided only in the forward region E1 located forward of the place 19 on the four side surfaces (the first main surface 21, the second main surface 23, the first side surface 111, and the second side surface 113) of the element body 70 where the protection layer 17 has the largest thickness Dmax. Therefore, it is possible to prevent the condensed water from reaching the vertexes 74 by the spaces 18. Also, it is possible to restrain deterioration in adhesion between the protection layer 17 and the element body 70 in a rearward region E2 located rearward of the place 19.

Additionally, the protection layer 17 is in contact with at least a portion of the forward end surface 127 and is in contact with at least a portion of the four side surfaces (the first main surface 21, the second main surface 23, the first side surface 111, and the second side surface 113) in the forward region E1. Thus, even though the spaces 18 formed to separate the element body 70 and the protection layer 17 are provided in the forward region E1, it is possible to restrain deterioration in adhesion between the protection layer 17 and the element body 70 in the forward region E1. In particular, since the protection layer 17 is in contact with at least a portion of the four side surfaces of the element body 70 in the forward region E1, it is possible to further restrain deterioration in adhesion between the protection layer 17 and the element body 70 in the forward region E1.

Also, in the forward region E1, the element body 70 is in contact with the protection layer 17 through a portion of the forward end surface 127 and portions of the side surfaces (the first main surface 21, the second main surface 23, the first side surface 111, and the second side surface 113) in the forward region E1, the total surface area of the portion of the forward end surface 127 and the portions of the side surfaces being half the total surface area of the forward end surface 127 and the side surfaces. Since a sufficient contact area can be secured between the element body 70 and the protection layer 17 in the forward region E1, separation of the protection layer 17 from the element body 70 becomes more unlikely to arise.

As shown in FIG. 4, the maximum width W1 of each space 18 which is measured from the corresponding vertex 74 in the width direction of the element body 70 is less than half the width W2 of the element body 70. Notably, in the case where the vertex 74 is not a point but one side of a chamfered portion, the distance between a vertex present before formation of the chamfered portion and an end portion of the space 18 closest to the center of the element body 70 in the width direction thereof is used as the maximum width W1. Also, in the case where a plurality of the spaces 18 are provided as shown in FIG. 4, it is preferred that the maximum widths W1 of all the spaces 18 be less than half the width W2 of the element body 70.

When the maximum width W1 of each space 18 is less than half the width W2 of the element body 70, it is possible to prevent the spaces 18 from occupying an excessively large area on the outer surface of the forward region E1 of the element body 70, to thereby secure a sufficiently large contact area between the element body 70 and the protection layer 17.

Also, as shown in FIG. 4, the maximum thickness T1 of each space 18 which is measured from the corresponding vertex 74 in the thickness direction of the element body 70 is less than half the thickness T2 of the element body 70. Notably, in the case where the vertex 74 is not a point but one side of a chamfered portion, the distance between a vertex present before formation of the chamfered portion and an end portion of the space 18 closest to the center of the element body 70 in the thickness direction thereof is used as the maximum thickness T1. Also, in the case where a plurality of the spaces 18 are provided as shown in FIG. 4, it is preferred that the maximum thicknesses T1 of all the spaces 18 be less than half the thickness T2 of the element body 70.

When the maximum thickness T1 of each space 18 is less than half the thickness T2 of the element body 70, it is possible to prevent the spaces 18 from occupying an excessively large area on the outer surface of the forward region E1 of the element body 70, to thereby secure a sufficiently large contact area between the element body 70 and the protection layer 17.

1-3. Method of Manufacturing Gas Sensor

A method of manufacturing the air/fuel ratio sensor 1 of the present embodiment will be described with reference to FIGS. 6 and 7.

Figure 6:
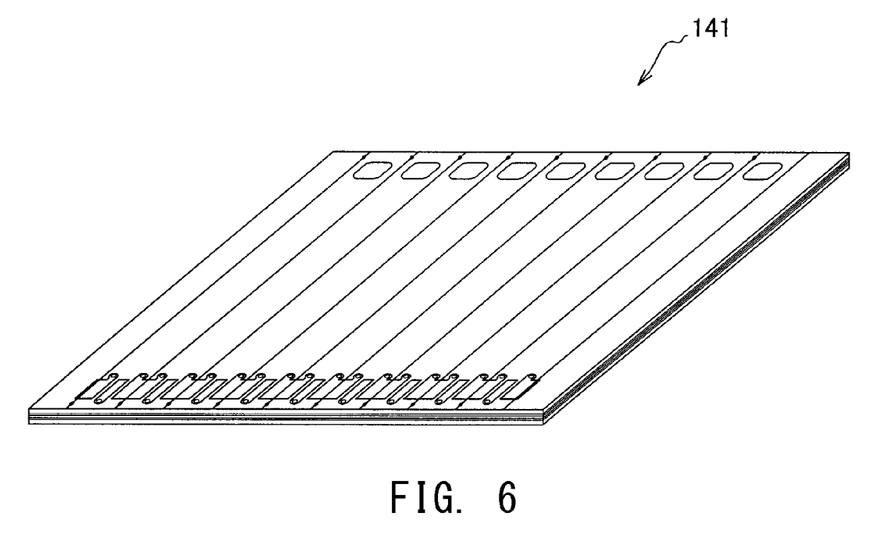
FIG. 6 is an explanatory view regarding a method of manufacturing green compacts of the gas sensor elements.

FIG. 6 is an explanatory view regarding a method of manufacturing a green compact 141 of the gas sensor elements. FIG. 7 is an explanatory view showing the gas sensor element in the middle of manufacture.

In manufacture of the gas sensor element 7, first, an uncompressed laminate is prepared by laminating together publicly known various materials used to form the gas sensor element 7; specifically, green solid electrolyte sheets used to form the solid electrolyte bodies 75 and 83 of the element 71, green insulating sheets used to form the insulating substrates 97, 101, and 103 of the heater 73 and the element 71, among others. The uncompressed laminate has green electrode pads which are to become the electrode pads 25, 27, 29, 31, and 33, among others, formed beforehand therein.

Among these materials, for example, the green solid electrolyte sheet is formed in the following manner. First, alumina powder, butyral resin, etc., are added to ceramic powder which predominantly contains zirconia. Into the resultant mixture, a mixed solvent (toluene and methyl ethyl ketone) is mixed, thereby forming slurry. The slurry is formed into a sheet by a doctor blade process, and the mixed solvent is volatilized, thereby yielding the green solid electrolyte sheet.

Also, the green insulating sheet is formed in the following manner. First, butyral resin and dibutyl phthalate are added to ceramic powder which predominantly contains alumina. Into the resultant mixture, a mixed solvent (toluene and methyl ethyl ketone) is mixed, thereby forming slurry. The slurry is formed into a sheet by the doctor blade process, and the mixed solvent is volatilized, thereby yielding the green insulating sheet.

Furthermore, green diffusion controlling portions are formed in the following manner. First, 100 mass % alumina powder and a plasticizer are wet-mixed, thereby forming slurry in which the alumina powder and the plasticizer are diffused. The plasticizer contains butyral resin and DBP. The slurry is applied to regions where the diffusion controlling portions 95 and the ventilating portion 99 are to be formed through firing, thereby forming the green diffusion controlling portions.

Then, the uncompressed laminate is compressed under a pressure of 1 MPa, thereby yielding the green compact 141 as shown in FIG. 6. A method of manufacturing the uncompressed laminate is similar to a publicly known method of manufacturing a gas sensor element; therefore, detailed description of the method is omitted.

The green compact 141 yielded through application of pressure is cut into a plurality of (e.g., ten) green laminates, each having a predetermined size substantially identical to that of the element 71 and the heater 73 of the gas sensor element 7.

Figure 7:
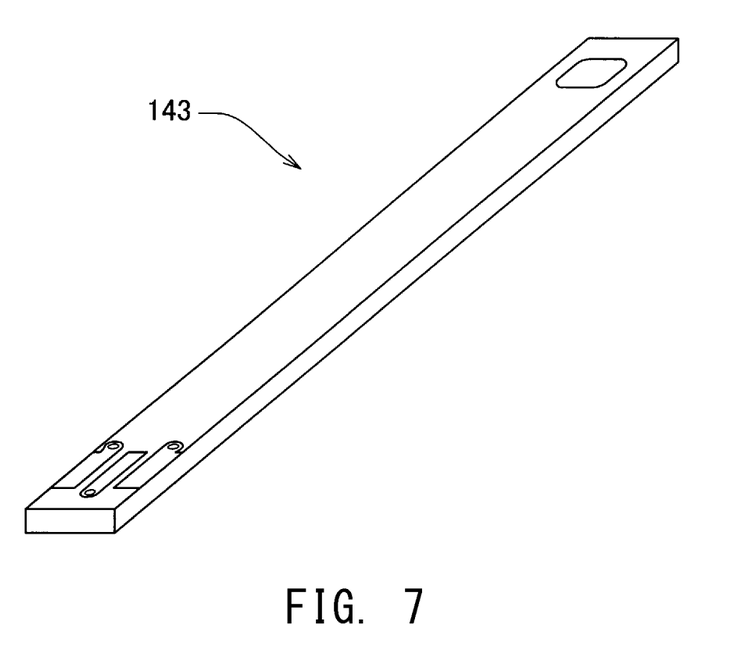
FIG. 7 is an explanatory view showing the gas sensor element in the middle of manufacture.

Subsequently, the green laminate is debindered and is, furthermore, subjected to regular firing at 1,500° C. for one hour, thereby yielding a fired laminate 143 as shown in FIG. 7.

Next, the fired laminate 143 is chamfered at its longitudinally extending four edges (the first edge H1, the second edge H2, the third edge H3, and the fourth edge H4), thereby forming the first long-edge chamfer 121, the second long-edge chamfer 122, the third long-edge chamfer 123, and the fourth long-edge chamfer 124 (see FIGS. 2 and 4). Specifically, the longitudinally extending four edges (the first edge H1, the second edge H2, the third edge H3, and the fourth edge H4) are applied to grindstone for well-known chamfering. Thus, the element body 70 is yielded.

After the element body 70 is yielded as mentioned above, a green protection layer is formed around a forward end portion of the element body 70. The green protection layer becomes the protection layer 17 having the spaces 18 (see FIGS. 2, 4, and 5) through firing.

Figure 8:
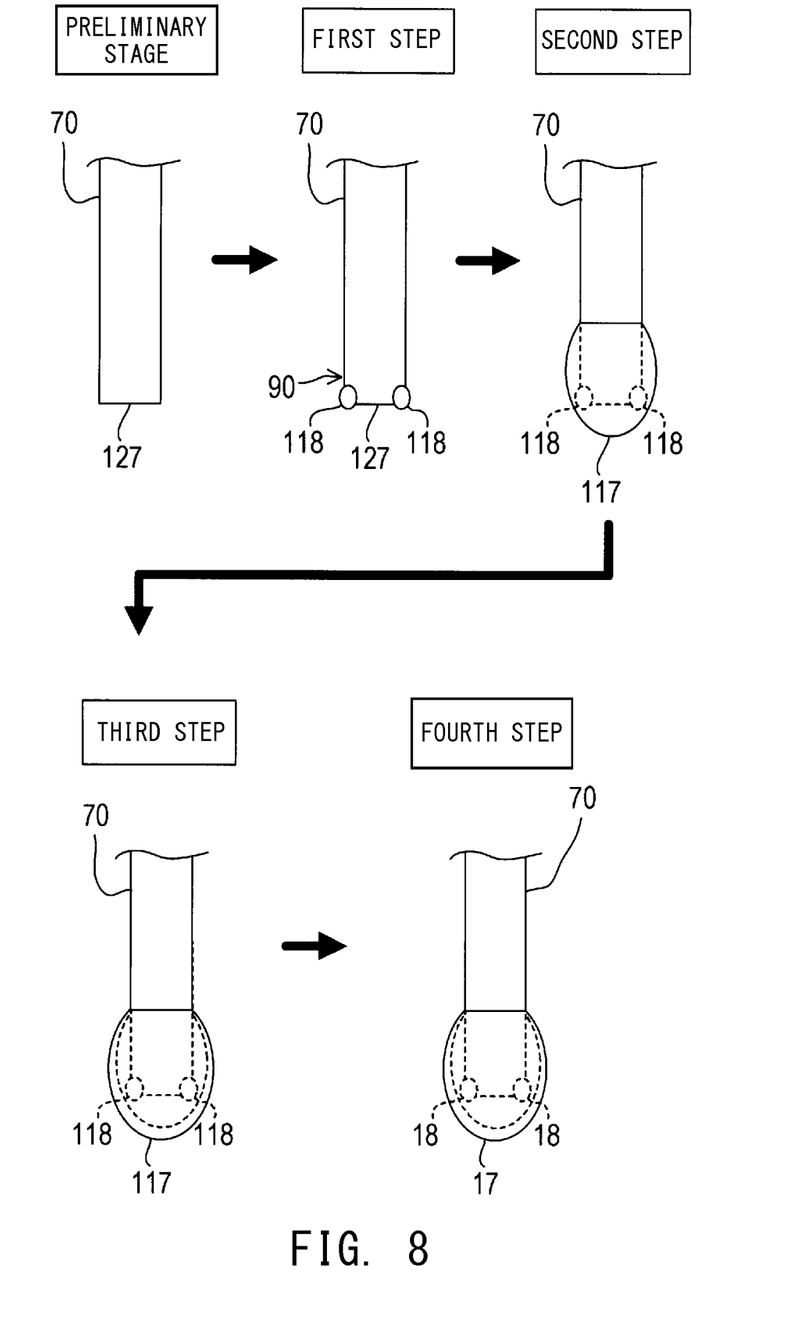
FIG. 8 is an explanatory view showing steps of forming a green protection layer.

FIG. 8 is an explanatory view showing steps of forming a green protection layer 117 on the element body 70, and yielding the protection layer 17 by performing heat treatment on the green protection layer 117.

In a stage before formation of the green protection layer 117, the element body 70 does not have a volatile solvent 118 and the green protection layer 117 thereon.

First, in the first step, the volatile solvent 118 (e.g., ethanol, propylene glycol, or butyl carbitol) is applied to the four vertexes 74 of the forward end surface 127 of the element body 70. At that time, the volatile solvent 118 is applied to each vertex 74 in such a manner that the volatile solvent 118 extends along three surfaces of the element body 70 which define the vertex 74. Namely, in the first step, the volatile solvent 118 is applied to regions which are to become the spaces 18 after firing.

In the next second step, while the applied volatile solvent 118 remains, a forward end portion of the element body 70 is dipped into protection layer slurry in a slurry container, thereby forming a portion of a green protection layer 117 on the element body 70 in such a manner as to cover at least the detecting section 90.

In the subsequent third step, the forward end portion of the element body 70 is again dipped into the protection layer slurry in the slurry container, thereby forming another portion of the green protection layer 117. Subsequently, dipping is performed a predetermined number of times, thereby completing formation of the green protection layer 117 having a predetermined thickness.

In the subsequent fourth step, the green protection layer 117 is subjected to heat treatment. Specifically, the element body 70 having the green protection layer 117 formed thereon is subjected to heat treatment at a temperature of 1,000° C. for three hours, thereby yielding the gas sensor element 7 on which the protection layer 17 having the spaces 18 is formed. The green protection layer 117 is fired to thereby become the protection layer 17, and regions where the volatile solvent 118 is applied become the spaces 18.

During the period from application of the volatile solvent 118 in the first step to heat treatment of the green protection layer 117 in the fourth step, the volatile solvent 118 gradually volatilizes, thereby forming the spaces 18 between the element body 70 and the protection layer 17.

The thus-formed gas sensor element 7 is assembled to the metallic shell 5 in a subassembling step.

Specifically, in this subassembling step, the gas sensor element 7 manufactured by the above method is inserted into the metallic holder 51; furthermore, the gas sensor element 7 is fixed in place by the ceramic holder 41 and the talc ring 43, thereby forming a subassembly. Subsequently, while the subassembly is fixed to the metallic shell 5, and an axially rear end portion of the gas sensor element 7 is inserted through the talc ring 45 and the ceramic sleeve 9, these members are inserted into the metallic shell 5.

Then, the rear end portion 47 of the metallic shell 5 is crimped to the ceramic sleeve 9, thereby yielding a lower subassembly. The protector 55 is attached beforehand to the lower subassembly.

Meanwhile, the outer tube 57, the separator 13, the grommet 61, etc., are assembled together, thereby yielding an upper subassembly. Then, the lower subassembly and the upper subassembly are joined together, thereby yielding the air/fuel ratio sensor 1.

1-4. Comparative Test

In order to verify resistance to adhesion of water of the gas sensor element of the present invention, a water adhesion test was conducted. The test results will be described below.

In this test, a predetermined amount of water was adhered to the protection layer 17 of the gas sensor element 7 to check to see whether or not the element body 70 was broken. A sensor signal Ip output from the gas sensor element 7 was monitored. When a variation of the monitored sensor signal Ip was 1% or more in relation to the sensor signal Ip before adhesion of water, the element body 70 was considered to have broken. When a variation of the monitored sensor signal Ip was less than 1% in relation to the sensor signal Ip before adhesion of water, the element body 70 was considered to be free from breakage.

In this test, a gas sensor element having no spaces between the protection layer and the element body was prepared as a Comparative Example and was subjected to the water adhesion test. The water adhesion test was conducted on two samples (Examples 1 and 2) of the present invention which differed in the thickness of the protection layer at corners of the forward end of the gas sensor element, and on two samples (Comparative Examples 1 and 2) which differed in the thickness of the protection layer at corners of the forward end of the gas sensor element.

Water to be adhered was increased at five stages (1 μL, 2 μL, 5 μL, 7 μL, and 10 μL) in the test. When a certain sample suffered breakage of the element body at a certain amount of adhered water, the test on the sample was discontinued at that stage of the amount of water.

Table 1 shows the test results. In Table 1, "Good" appearing in the column "Result of water adhesion test" indicates that the element body is free from breakage, and "Poor" indicates that the element body was broken.

TABLE 1

| Sample | Existence of space | Result of water adhesion test | | | | | Thickness of protection layer [μm] |
|---|---|---|---|---|---|---|---|
| | | 1 μL | 2 μL | 5 μL | 7 μL | 10 μL | |
| Example 1 | Yes | Good | Good | Good | Good | Good | 344.4 |
| Example 2 | Yes | Good | Good | Good | Good | Good | 354.5 |
| Comp. Example 1 | No | Good | Poor | — | — | — | 330.4 |
| Comp. Example 2 | No | Good | Good | Poor | — | — | 351.2 |

According to the test results, Examples 1 and 2 are free from breakage of the element body 70 at all stages of the amount of adhered water (1 μl, to 10 μL). Comparative Example 1 suffered breakage of the element body at an amount of adhered water of 2 μL, and Comparative Example 2 suffered breakage of the element body at an amount of adhered water of 5 μL.

Thus, as compared with a gas sensor element which does not have the spaces, the gas sensor element 7 of the present invention is less likely to suffer breakage of the element body which otherwise result from thermal shock stemming from adhesion of water, and therefore has excellent resistance to adhesion of water.

1-5. Effects

As described above, the gas sensor element 7 in the air/fuel ratio sensor 1 of the present embodiment has the spaces 18 between the protection layer 17 and the element body 70.

The gas sensor element 7 has at least four spaces 18 which correspond to the four vertexes 74 of the forward end of the element body 70. Each space 18 is provided on the corresponding vertex 74 such that the space 18 extends over three surfaces of the element body 70 which define the vertex 74. Also, the spaces 18 are formed only in the forward region E1 located forward of the place 19 (where the protection layer 17 has the largest thickness Dmax) on the side surfaces (the first main surface 21, the second main surface 23, the first side surface 111, and the second side surface 113) of the element body 70.

In the gas sensor element 7, the spaces 18 for separating the element body 70 and the protection layer 17 are formed on the vertexes 74 of the forward end of the element body 70, at which the thickness of the protection layer 17 is likely to become small, such that each space 18 extends over three surfaces of the element body 70 which define the corresponding vertex 74. Therefore, even though the thicknesses L1 to L4 of the protection layer 17 in the vicinity of the vertexes 74 are small, there can be restrained breakage of the vertexes 74 of the forward end of the element body 70 which could otherwise result from thermal shock stemming from adhesion of water.

That is, the protection layer 17 of the gas sensor element 7 can be reduced in thickness and thus in heat capacity as compared with a conventional protection layer formed by a dipping process.

Also, the spaces 18 are formed only in the forward region E1 located forward of the place 19 on the side surfaces of the element body 70 where the protection layer 17 has the largest thickness Dmax. By virtue of this feature, it is possible to prevent condensed water from reaching the vertexes 74 by the spaces 18, and is also possible to restrain deterioration in adhesion between the protection layer 17 and the element body 70 in the rear region E2 located rearward of the place 19.

Additionally, the protection layer 17 is in contact with at least a portion of the forward end surface 127 of the element body 70 and is in contact with at least a portion of the four side surfaces (the first main surface 21, the second main surface 23, the first side surface 111, and the second side surface 113) in the forward region E1. Thus, although the spaces 18 formed in such a manner as to separate the element body 70 and the protection layer 17 are provided in the forward region E1, deterioration in adhesion between the protection layer 17 and the element body 70 can be restrained even in the forward region E1.

1-6. Correspondence Between Claims and Present Embodiment

Correspondence in wording between claims and the present embodiment will be described below.

The first main surface 21, the second main surface 23, the first side surface 111, and the second side surface 113 correspond to the side surfaces of the element body. The air/fuel ratio sensor 1 corresponds to the gas sensor.

The first step corresponds to the solvent disposing step; the second and third steps correspond to the protection layer forming step; and the fourth step corresponds to the heat treatment step.

2. Another Embodiment

While the present invention has been described with reference to the above embodiment, the present invention is not limited thereto, but may be embodied in various other forms without departing from the gist of the invention.

For example, the element body of the gas sensor element is not limited to the one in which the first edge H1, the second edge H2, the third edge H3, and the fourth edge H4 are chamfered. The element body can be configured such that none of the first edge H1, the second edge H2, the third edge H3, and the fourth edge H4 is chamfered.

Figure 9:
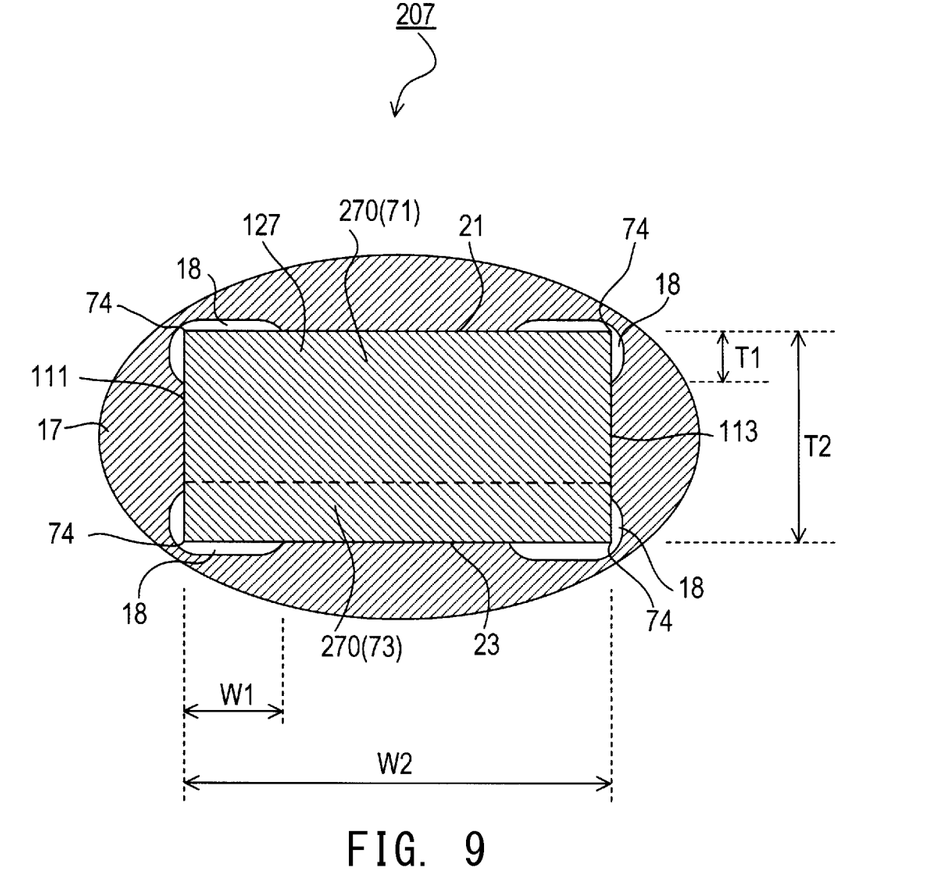
FIG. 9 is a sectional view showing a gas sensor element having an unchamfered element body.

FIG. 9 is a sectional view showing a second gas sensor element 207 having an unchamfered second element body 270, taken along the forward end surface 127 of the second element body 270. In the thus-configured second gas sensor element 207, each of the vertexes 74 assumes the form of a single point rather than a ridgeline. Therefore, the maximum width W1 and the maximum thickness T1 of each space 18 are determined as shown in FIG. 9.

The spaces are not necessarily provided on all of the four vertexes of the forward end surface of the element body as in the case of the first embodiment. For example, the spaces may be provided on three or fewer of the four vertexes. In certain usage of the gas sensor element, provision of a single space may be able to restrain thermal shock stemming from adhesion of water. In such a case, provision of a single space may be employed. In the case of provision of two or more spaces on the respective vertexes, the spaces may be provided at least on two diagonally located vertexes, respectively.

A single space is not necessarily provided on only a single vertex, but may be provided to extend between and over two vertexes.

In the case of provision of a large number of spaces or provision of large spaces, preferably, a sufficient contact area is provided between the protection layer and the element body. For example, through employment of contact between the protection layer and the element body at least half of the surface area of the forward end surface and the side surfaces in the forward region E1 of the element body, there can be implemented a gas sensor element in which separation of the protection layer from the element body is unlikely to arise.

DESCRIPTION OF REFERENCE NUMERALS

1: air/fuel ratio sensor; 5: metallic shell, 7: gas sensor element; 9: ceramic sleeve; 11: insertion hole; 17: protection layer; 18: space; 19: place; 21: first main surface; 23: second main surface; 70: element body; 74: vertex; 81: oxygen concentration cell; 89: oxygen pump cell; 90: detecting section; 91: gas measuring chamber; 94: gas inlet; 95: diffusion controlling portions; 105: heat generating resistor pattern; 111: first side surface; 113: second side surface; 117: green protection layer; 118: volatile solvent; 127: forward end surface; 143: fired laminate; 207: second gas sensor element; 270: second element body.

What is claimed is:

1. A gas sensor element comprising:
an element body having a substantially rectangular-parallelepiped shape extending along a longitudinal axis, a forward end surface through which the longitudinal axis extends, and four side surfaces adjacent to the forward end surface so as to define four vertexes, and including a detecting section for detecting a particular gas; and
a protection layer located on the forward end surface and the four side surfaces of the element body in such a manner as to cover at least the detecting section, the protection layer having a largest thickness perpendicular to the element body at a place on the side surfaces of the element body and formed in a porous manner;
wherein:
the element body and the protection layer define at least one space therebetween in a forward region located entirely forward of a place of the largest thickness of the protection layer;
the space is positioned over at least one of the four vertexes such that the space extends over three surfaces of the element body which define the one of the four vertexes; and
the protection layer is in contact with at least a portion of the forward end surface and is in contact with at least a portion of the four side surfaces in the forward region.

2. The gas sensor element according to claim 1, wherein the protection layer is in contact with at least a portion of each of the four side surfaces in the forward region.

3. The gas sensor element according to claim 1, wherein the protection layer is in contact with a portion of the forward end surface and portions of the four side surfaces in the forward region, and the total surface area of the portion of the forward end surface and the portions of the side surfaces is half of the total surface area of the forward end surface and the four side surfaces in the forward region.

4. The gas sensor element according to claim 1, wherein the space is positioned over only one of the four vertexes.

5. The gas sensor element according to claim 1, wherein the element body and the protection layer define at least two spaces therebetween.

6. The gas sensor element according to claim 5, wherein the at least two spaces are respectively positioned over at least two diagonally located vertexes of the four vertexes.

7. The gas sensor element according to claim 1, wherein a maximum width of the at least one space measured from the vertex in a width direction of the element body is less than half a width of the element body.

8. The gas sensor element according to claim 1, wherein a maximum thickness of the space measured from the vertex in a thickness direction of the element body is less than half a thickness of the element body.

9. A gas sensor comprising the gas sensor element according to claim 1 adapted to detect the particular gas.

10. A method of manufacturing a gas sensor element which comprises an element body having a substantially rectangular-parallelepiped shape extending along a longitudinal axis, a forward end surface through which the longitudinal axis extends, and four side surfaces adjacent to the forward end surface so as to define four vertexes, and including a detecting section for detecting a particular gas, and a protection layer located on the forward end surface and four side surfaces of the element body in such a manner as to cover at least the detecting section, the protection layer having a largest thickness perpendicular to the element body at a place on the side surfaces of the element body and formed in a porous manner,
the element body and the protection layer defining at least one space therebetween in a forward region located entirely forward of the place of the largest thickness of the protection layer;
the space being positioned over at least one of the four vertexes such that the space extends over three surfaces of the element body which define the one of the four vertexes; and
the protection layer being in contact with at least a portion of the forward end surface and being in contact with at least a portion of the four side surfaces in the forward region,
the method comprising:
a solvent disposing step of disposing a volatile solvent on an outer surface of the element body in a region where the space is to be formed,
a protection layer forming step of forming, on the element body on which the volatile solvent remains, a green protection layer which is to become the protection layer through heat treatment, in such a manner as to cover at least the detecting section, and
a heat treatment step of performing heat treatment on the element body on which the green protection layer is formed, thereby forming the protection layer,
wherein the volatile solvent is volatilized in a period from start of the solvent disposing step to end of the heat treatment step, thereby forming the space.

* * * * *